(12) United States Patent
Specht et al.

(10) Patent No.: US 7,462,237 B2
(45) Date of Patent: Dec. 9, 2008

(54) SYSTEMS AND METHODS FOR GENERATING IMAGES OF CRYSTALS

(75) Inventors: Peter Nollert-von Specht, Bainbridge Island, WA (US); Mark B. Mixon, Poulsbo, WA (US)

(73) Assignee: deCODE biostructures, Inc., Bainbridge Island, WA (US)

( * ) Notice: Subject to any disclaimer, the term of this patent is extended or adjusted under 35 U.S.C. 154(b) by 209 days.

(21) Appl. No.: 11/170,758

(22) Filed: Jun. 28, 2005

(65) Prior Publication Data

US 2006/0021563 A1 Feb. 2, 2006

Related U.S. Application Data

(60) Provisional application No. 60/584,110, filed on Jun. 30, 2004.

(51) Int. Cl.
C30B 7/00 (2006.01)
(52) U.S. Cl. .............................. 117/1; 117/2; 117/200; 117/201; 117/202
(58) Field of Classification Search ................. 117/200, 117/201, 202, 1, 2
See application file for complete search history.

(56) References Cited

U.S. PATENT DOCUMENTS

| | | |
|---|---|---|
| 6,529,612 B1 | 3/2003 | Gester et al. |
| 6,673,639 B2 | 1/2004 | Wada |
| 2005/0112774 A1 * | 5/2005 | Gilbert et al. ............... 436/174 |
| 2005/0126505 A1 * | 6/2005 | Gallager et al. ............. 119/234 |

FOREIGN PATENT DOCUMENTS

JP 9052741 * 2/1997

OTHER PUBLICATIONS

Sazaki et al., "Mechanism of crystallization of enzyme protein", *Journal of Crystal Growth*, vol. 130(3-4) pp. 357-367, 1993 abstract only.*
CIE Technical Report 116-1995: Industrial Colour-Difference Evaluation, Commission Inernationale de L'Eclairage [International Commission on Illumination], Vienna, 1995.
Jurisica, I., et al., "Image Feature Extraction for Protein Crystallization: Integrating Image Analysis and Case-Based Reasoning," *Proceedings of the Thirteenth Innovative Applications of Artificial Intelligence Conference*, Seattle, Wash., Aug. 7-9, 2001, pp. 73-80.
McDonald, R., and K.J. Smith, "CIE94—A New Colour-Difference Formula," *Journal of the Society of Dyers and Colourists* 111:376-379, 1995.
Nollert, P., "From Test Tube to Plate: A Simple Procedure for the Rapid Preparation of Microcrystallization Experiments Using the Cubic Phase Method," *Journal of Applied Crystallography* 35:637-640, 2002.

* cited by examiner

*Primary Examiner*—Robert M Kunemund
(74) *Attorney, Agent, or Firm*—Christensen O'Connor Johnson Kindess PLLC

(57) ABSTRACT

The present invention provides computer-implementable systems and methods for generating images of crystals. The systems each include (a) a light source; (b) a rotatable first polarizing material; (c) a rotatable second polarizing material; (d) a light-capturing device; and (e) a software program executable on the computer-implementable system for analyzing electrical signals from the light-capturing device.

21 Claims, 6 Drawing Sheets

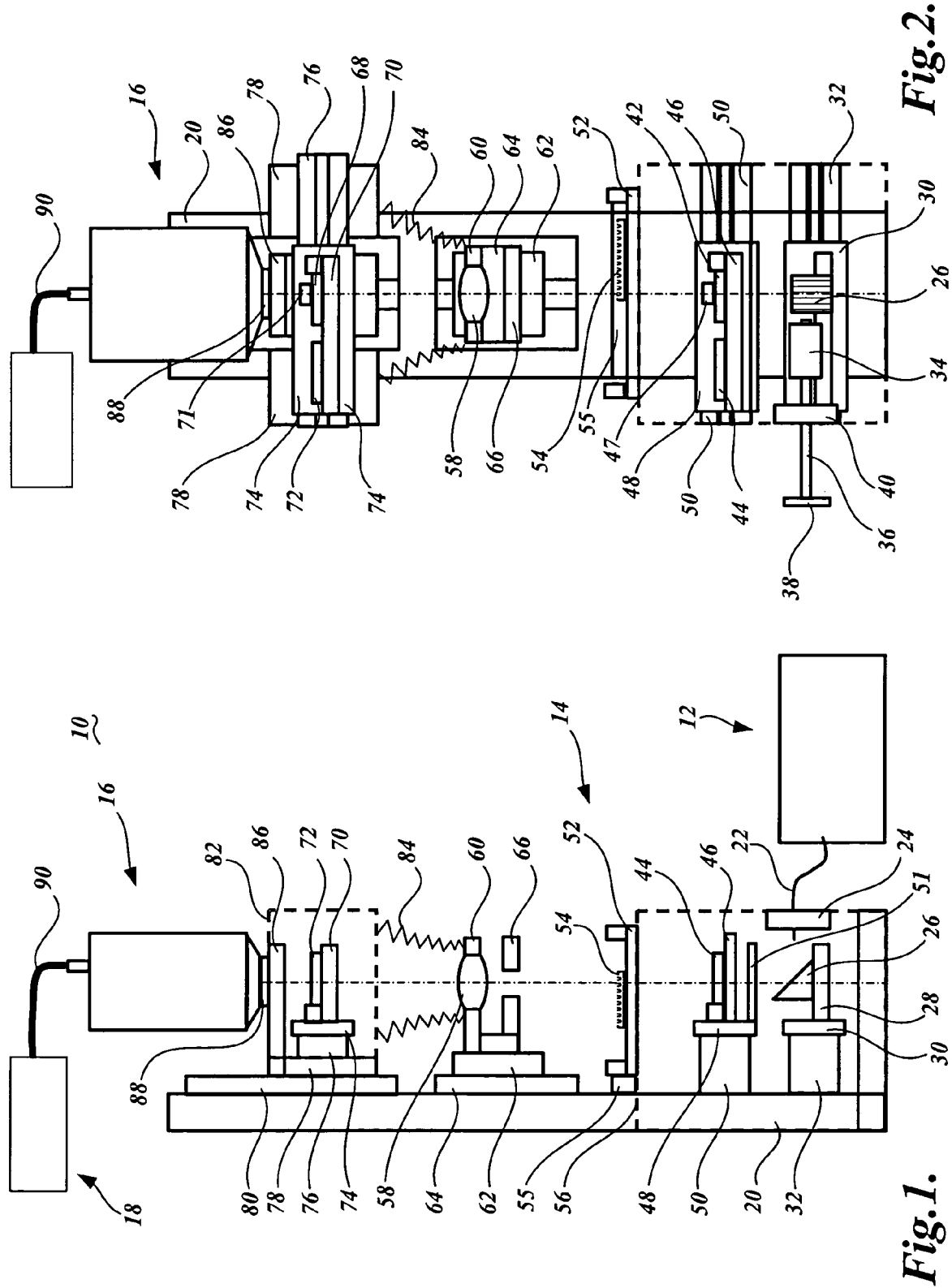

SYSTEMS AND METHODS FOR GENERATING IMAGES OF CRYSTALS

CROSS-REFERENCE TO RELATED APPLICATION

The present application claims the benefit of U.S. Provisional Patent Application No. 60/584,110, filed Jun. 30, 2004.

FIELD OF THE INVENTION

The present invention relates to systems, devices, and methods for generating images of crystals, such as protein crystals that form in a material that has optical properties that are similar to the optical properties of the crystals.

BACKGROUND OF THE INVENTION

X-ray crystallography is a technique that is used to determine the three-dimensional arrangement of atoms within protein molecules. The x-ray diffraction pattern of a protein crystal is analyzed to determine the three dimensional structure of the protein. The growth of protein crystals is a trial and error process. Often hundreds or thousands of experiments are carried out in order to determine conditions that promote the nucleation and growth of crystals of a particular protein. Most crystallization experiments are set up in plastic trays that contain many wells.

Proteins that exist, in vivo, embedded within a cell membrane are referred to as "membrane proteins". Examples of membrane proteins include ion channels and G-protein coupled receptors. Many membrane proteins are high-value drug targets for the pharmaceutical industry, and their three-dimensional structures would offer huge potential for the purpose of structure-based drug discovery and design. Unfortunately membrane proteins are difficult to crystallize, and as a consequence only approximately 30 high-resolution structures of different membrane proteins are currently available.

Traditionally, membrane protein crystals have been grown in solution from detergent/protein complexes. Matrices (e.g., silica gels and agarose gels) have also been used for the generation of crystals for x-ray diffraction experiments (Garcia-Ruiz, J. M., et al, "Teaching Protein Crystallization by the Gel Acupuncture Technique," *J. Chem. Edu.* 75:442-446 (1998); Biertupfel, C., et al., "Crystallization of Biological Macromolecules Using Agarose Gel," *Acta Cryst.* D58:1657-1659 (2002)). In such matrix-based experiments the protein is embedded in the gel-like material and a crystallization inducing agent is added. The gel reduces convection, in effect generating conditions that are close to crystallization at zero gravity, and in some cases provides a favorable environment for nucleation and growth of crystals (Rummel, G., et al., "Lipidic Cubic Phases: New Matrices for the Three-Dimensional Crystallization of Membrane Proteins," *J. Struct. Biol.* 121:1-11 (1998)). One such matrix is the so-called lipid cubic phase (LCP). The use of lipidic cubic phases as a crystallization matrix has provided high-quality crystals of several membrane proteins that could not be crystallized as detergent/protein complexes (Caffrey, M., "Membrane Protein Crystallization," *J. Struct. Biol.* 142(1):108-32 (2003)). Several soluble proteins have also been crystallized in an LCP matrix, suggesting that some soluble proteins that resisted crystallization using other crystallization methods may crystallize in an LCP matrix. So far, all membrane proteins crystallized in the lipidic cubic phase were colored (Chiu, M. L., et al., "Crystallization In Cubo: General Applicability to Membrane Proteins," *Acta Crystallographica D* 56:781-784 (2000)).

Protein crystallization experiments are usually carried out in containers (e.g., 96 well plastic crystallization trays) that permit physical contact between the protein matrix or solution with a crystallization inducing agent (a solution or a solid). The outcome of the experiment, "crystal" or "no crystal", is typically assessed by an operator via visual inspection using a microscope. For this purpose dissecting microscopes with bright field illumination, dark field illumination and polarization options are generally used. More advanced systems can automatically capture images of the experiments and store these in a database. The annotation of the experiment and the decision regarding the final result requires input from a human operator. Since this manual annotation is slow it creates a serious bottleneck when large numbers of crystallization setups are to be evaluated. Several automated systems have been devised to decrease the number of images that need to be inspected by the operator (Rupp, B., "High-Throughput Crystallography at an Affordable Cost: The TB Structural Genomics Consortium Crystallization Facility," *Acc. Chem. Res.* 36(3):173-81. 2003; Gester, T. E., et al., "Method for Acquiring, Storing and Analyzing Crystal Images", U.S. Pat. No. 6,529,612, 2003). These methods often carry out simple pre-selections (e.g., ignoring experiments where no changes have occurred throughout the experiment). In addition to such negative-selection procedures, image processing routines have been employed in order to identify crystals (Rupp, 2003, supra; Gester et al., 2003, supra). In virtually all cases these algorithms are based on edge detection algorithms and pattern recognition. Generally, these crystal scoring tools work well for clear-cut results and face challenges when the crystallization experiment contains small crystals, when the matrix is not perfectly transparent, or when precipitation occurs.

A number of problems are associated with crystallization of colorless membrane proteins in lipidic cubic phases. For example, low contrast due to the small difference in refractive indices of protein crystals and the surrounding lipidic phases (Nollert, P., "Microscope Detection Options for Colorless Protein Crystals Grown in Lipidic Cubic Phases," *J. Appl. Cryst.* 36(5). 2003); and an obscured matrix that causes poor visibility. This may be due to the formation of protein precipitate or due to lipid that may undergo a transition into non-transparent phases during the course of crystallization. Also, crystals may be very small and difficult to see.

The foregoing problems limit the applicability of the LCP-technology for colorless membrane proteins. The present patent application provides systems and methods that use the phenomenon of birefringence to facilitate detection of crystals and enhance their contrast within a matrix. The present invention can be applied to all crystallization experiments.

SUMMARY OF THE INVENTION

In one aspect, the present invention provides a computer-implementable system for generating images of crystals, the system comprising: (a) a light source; (b) a rotatable first polarizing material; (c) a rotatable second polarizing material; (d) a light-capturing device; and (e) a software program executable on the computer-implementable system for analyzing electrical signals from the light-capturing device, wherein, in operation, (1) light from the light source passes through the first polarizing material, then passes through a sample located between the first polarizing material and the second polarizing material, then passes through the second polarizing material and impinges on the light-capturing device to generate an image, the image comprising a red component, a green component and a blue component, in the form of an electrical signal that is transmitted to a computing device on which the software program is executing; and (2) the software program decomposes the image into its red, green and blue components, calculates differences between the red, green and blue components, and combines the differences to form a combined image.

In some embodiments of the system of the invention, the software program: (1) acquires from 1 to n sample images; (2) decomposes each of the sample images; (3) reduces the decomposed sample images to a series of two dimensional matrices; (4) submits each of the matrices to background correction; and (5) integrates the background corrected matrices to construct an enhanced image of the sample.

The present invention also provides computer-implementable methods for visualizing a birefringent crystal, as described more fully herein.

The systems and methods of the present invention can be used to visualize any type of crystal, including protein crystals present in a lipidic cubic phase material.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 shows an exemplary embodiment of a system of the present invention, including a microscope shown in cross-sectional side view.

FIG. 2 shows an exemplary embodiment of the system shown in FIG. 1, including a front view of the microscope.

DETAILED DESCRIPTION OF THE PREFERRED EMBODIMENT

Figure 3:
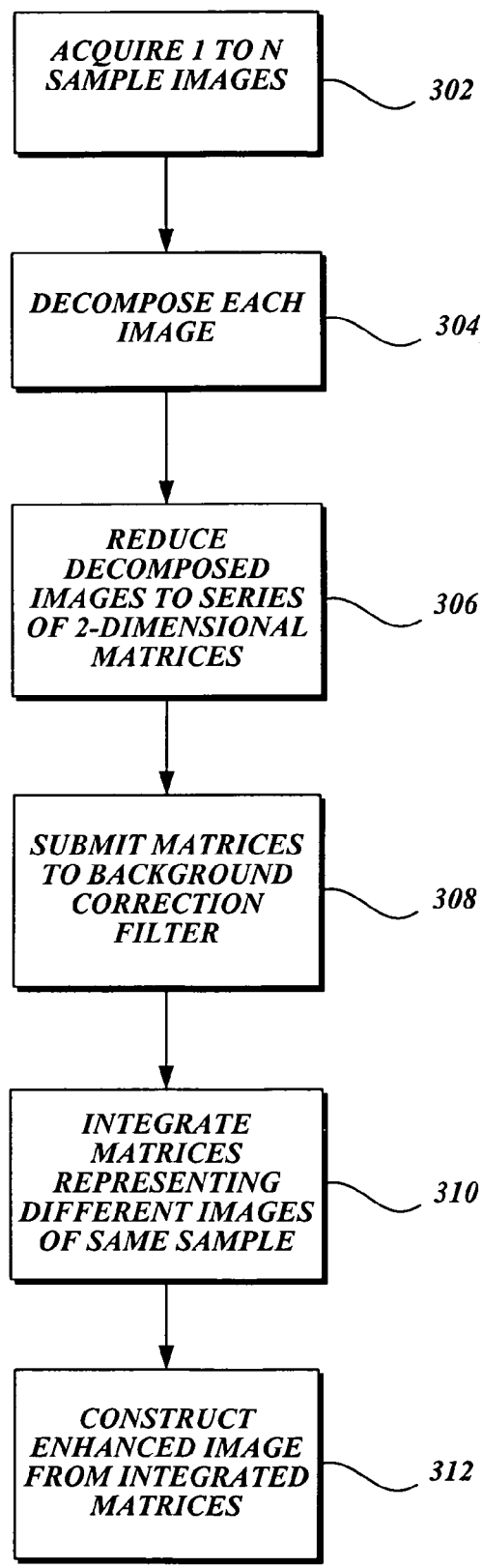
FIG. 3 is a block diagram depicting the major steps performed by the image analysis software used in the systems of the present invention.

As used herein, the term "extinction" refers to the phenomenon in which plane polarized light is completely, or almost completely, absorbed by two polarizing materials that are oriented so that their polarization axes are perpendicular with respect to each other.

In one aspect, the present invention provides computer-implementable systems for generating images of crystals. The systems each include: (a) a light source; (b) a rotatable first polarizing material; (c) a rotatable second polarizing material; (d) a light-capturing device; and (e) a software program executable on the computer-implementable system for analyzing electrical signals from the light-capturing device, wherein, in operation, (1) light from the light source passes through the first polarizing material, then passes through a sample located between the first polarizing material and the second polarizing material, then passes through the second polarizing material and impinges on the light-capturing device to generate an image, the image comprising a red component, a green component and a blue component, in the form of an electrical signal that is transmitted to a computing device on which the software program is executing; and (2) the software program decomposes the image into its red, green and blue components, calculates differences between the red, green and blue components, and combines the differences to form a combined image.

Light sources that are useful in the systems of the invention produce white light (having a wavelength in the range of from about 400 nm to about 800 nm) emitted by either an incandescent bulb or light emitting diode (LED). A light filter may be used to provide light with a desired wavelength and associated band width (e.g., Red filter 2350.081 sold by Volpi AG, Wiesenstrasse 33, CH-8952 Schlieren, Switzerland). An example of an incandescent light source is a Volpi KL150 (available from Volpi AG, Wiesenstrasse 33, CH-8952 Schlieren, Switzerland).

Polarizing materials useful in the practice of the invention polarize light. Some polarizing materials useful in the practice of the invention are birefringent. Some polarizing materials useful in the practice of the invention are circular light polarizing materials, and other polarizing materials useful in the practice of the invention are linear light polarizing materials. Examples of useful polarizing materials include Polaroid sheet filters, such as linear polarizer HN22 sold by 3M Corporation (3M Center, St. Paul, Minn. 55144-1000, USA).

The polarizing materials are rotatable about an axis of rotation that is at a 90 angle to the plane of the polarizing material. The polarizing materials are typically thin sheets of polarizing material that can be rotated in the plane of the sheet. While the sheet of material is being rotated the principal axis of the sheet remains parallel to the axis of rotation.

Light-capturing devices useful in the systems of the present invention capture light that has traveled through the first polarizing material, then through a sample (such as a sample of lipid cubic phase material containing crystals), then through the second polarizing material. Examples of useful light-capturing devices include devices (that can be arranged in two-dimensional arrays) that can capture and record visible light, such as CCD cameras, for example the Spot Insight QE Color Mosaic sold by Diagnostic Instruments, Inc., 6540 Burroghs St. Sterling Heights, Mich. 48314-2133, USA. The light-capturing device generates an image in the form of an electrical signal that is transmitted to a computer on which is executed a software program for analysis of the image as described herein.

FIG. 1 shows an exemplary embodiment of a system 10 of the present invention. System 10 includes a light source 12, a microscope 14 (shown, to facilitate explanation, as a cross-sectional side view in FIG. 1), a light-capturing device 16, and a computing device 18. A software program executes on computing device 18. The software program analyzes electrical signals from light-capturing device 16.

Microscope 14 includes an L-shaped bracket 20 that supports the components of microscope 14. A fiber optic bundle 22 connects light source 12 to a bushing fixture 24 which is part of microscope 14. Microscope 14 includes a reflecting prism 26 that reflects light from fiber optic bundle 22. Reflecting prism 26 is supported on prism support 28 that is attached to a stage 30. Stage 30 is attached to a set of motorized linear positioning rails 32.

As shown in the front view of microscope 14 shown in FIG. 2, microscope 14 also includes a reflector 34 that is mounted on an axle 36 that can be rotated by manually rotating a wheel 38. Microscope 14 also includes a guide 40 for axle 36. Guide 40 is attached to stage 30. Motorized linear positioning rails 32 allow horizontal movement of prism 26 and reflector 34 into either of two positions to allow light, from light source 12, to strike either prism 26 or reflector 34.

Also as shown in FIG. 2, microscope 14 includes a first polarization filter 42 (that is a linear or circular polarizing filter) and a first optical compensation filter 44 that are both supported on a support 46. First polarization filter 42 is rotated by a first motorized rotation stage 47 (such as the motorized rotation stage SGSP-120YAW sold by Sigma KOKI Co. LTD, 1-19-9, Midori, Sumida-ku, Tokyo, 130-0021, Japan). Support 46 is attached to a second stage 48 that is attached to a second set of motorized linear positioning rails 50 that allow horizontal movement of first polarization filter 42 and first optical compensation filter 44. Motorized linear positioning rails 50 are attached to L-shaped bracket 20. A receptacle 51 for a light filter is also attached to second stage 48. Different light filters (e.g., a red filter or blue filter) can be inserted into receptacle 51 to produce a beam of light having a desired color. Again by way of example, waveplates (e.g., lambda/4 or lamda/2 wave retardation plates) can be inserted into receptacle 51 to increase the polarization contrast of low polarization contrast objects.

Microscope 14 also includes a mobile stage 52 that supports a sample holder 54, such as a crystallization tray comprising numerous wells for holding samples (e.g., a CombiClover™ Junior plate, available from deCode biostructures, 7869 NE Day Road West, Bainbridge Island, Wash. 98110, USA). It is understood that sample holder 54 is not a part of system 10, but is shown for the purpose of illustration and explanation. Mobile stage 52 is attached to a set of motorized stage positioning rails 55 that move sample holder 54 in a horizontal plane to position a portion of sample holder 54 in the path of the light beam exiting first polarization filter 42 or first optical compensation filter 44. Motorized stage positioning rails 55 are attached to L-shaped bracket 20. A light-proof housing 56 encloses prism 26, first polarization filter 42, and first optical compensation filter 44.

Microscope 14 also includes a lens 58 that is held in place by a lens mount 60. Lens mount 60 is attached to a third stage 62 that is attached to a vertical lens positioning rail 64 that moves lens 58 up or down (thereby permitting adjustment of magnification of the sample image, for example in the range of from 1× to 5× magnification). A controllable aperture 66 regulates the amount of light reaching lens 58. Controllable aperture 66 is supported by third stage 62.

Microscope 14 also includes a second motorized polarization filter 68 (e.g., a linear polarizing filter) that is supported by a second support 70. Second motorized polarization filter 68 is rotated by a second motorized rotation stage 71 (such as the motorized rotation stage SGSP-120YAW sold by Sigma KOKI Co. LTD, 1-19-9, Midori, Sumida-ku, Tokyo, 130-0021, Japan). Second support 70 also supports a second optical compensation filter 72. Second support 70 is attached to a fourth stage 74 that is attached to a horizontal motorized linear positioning rail 76 that allows horizontal movement of second motorized polarization filter 68 and second optical compensation filter 72. A fifth stage 78 permits vertical movement of horizontal polarization rail 76. Fifth stage 78 moves along a vertical positioning rail 80. A light-proof housing 82 (shown in outline in FIG. 1) encloses second motorized polarization filter 68 and second optical compensation filter 72.

A flexible shroud 84 extends from light-proof housing 82 to lens mount 60. A C-mount 86 supports camera 16. An optional image multiplexer prism 88 (or image splitter) is disposed between camera 16 and second motorized polarization filter 68. Image multiplexer prism 88 (or image splitter) permits multiple images of the same object to be recorded. A cable 90 (e.g., a USB2 cable) connects camera 16 with computing device 18.

In operation, fiber optic bundle 22 guides light from light source 12 to either reflecting prism 26 or reflector 34. Bushing fixture 24 can be used to manually adjust the position of fiber optic bundle 22. Prism support 28 moves along motorized linear positioning rails 32 to position either reflecting prism 26 or reflector 34, as desired, in the path of light emanating from fiber optic bundle 22. Prism 26 can be used to illuminate an object at a fixed angle (e.g., 90 degree angle between light exiting fiber optic bundle 22 and light traveling towards the object to be illuminated). Reflector 34 is mobile, and can be rotated to deflect light in a way to make it strike an object from the side. Such manipulation of the reflector 34 can be used to visualize objects under pseudo-dark field illumination. Typically, prism 26 is used when first polarization filter 42 and second polarization filter 68 are in the light path, whereas reflector 34 is used when first polarization filter 42 and second polarization filter 68 are not in the light path and images are obtained from crystals that emphasize their crystal facets.

The movement of prism support 28 is controlled by a computer. The angle of reflector 34 relative to the beam of light emanating from fiber optic bundle 22 is controlled by manually rotating wheel 38. Thus, for example, adjustment of the angle of reflector 34 permits illumination of samples at an oblique angle, thereby producing pseudo-darkfield illumination.

Light reflected by reflecting prism 26 or reflector 34 is directed through either first motorized polarization filter 42 or first motorized optical compensation filter 44, and then impinges on a sample (e.g., crystals) in sample holder 54. Horizontal movement of motorized linear positioning rails 32 causes horizontal movement of support 28 thereby moving either first motorized polarization filter 42 or first motorized optical compensation filter 44 into the path of light from light source 12. First optical compensation filter 44 compensates for the optical effects of first polarization filter 42, and avoids the need to adjust focus when first polarization filter 42 is removed from the path of the light from light source 12. First polarization filter 42 can be rotated about its optical axis. In embodiments of the invention wherein first polarization filter 42 is a flat sheet of polarizing material, rotation is parallel to the plane of first polarization filter 42. The axis of rotation is parallel to the path of light entering first polarization filter 42 from light source 12.

Light that is transmitted through the sample passes through controllable aperture 66 which is manually operated and can be adjusted to permit more or less light to reach lens 58, thereby permitting adjustment for the depth of field and light intensity. Lens 58 magnifies and focuses the image of the sample onto camera 16. In one embodiment, lens 58 is a plan apochromat with a focal length of 35 mm.

Light that passes through lens 58 then passes through either second motorized polarization filter 68 or second optical compensation filter 72. Movement of horizontal motorized linear positioning rail 76 causes horizontal movement of second support 70 thereby moving either second motorized polarization filter 68 or second optical compensation filter 72 into the path of light from lens 58. Fifth stage 78 permits vertical movement of horizontal motorized linear positioning rail 76. Movement of fifth stage 78 along vertical positioning rail 80 causes vertical movement of second motorized polarization filter 68 and second optical compensation filter 72.

Second polarization filter 68 can be rotated about its optical axis. In embodiments of the invention wherein second polarization filter 68 is a flat sheet of polarizing material, rotation is parallel to the plane of second polarization filter 68. The axis of rotation is parallel to the path of light entering second polarization filter 68 from light source 12.

Light that passes through second motorized polarization filter 68, or through second optical compensation filter 72, then enters camera 16 and generates an electrical signal that is transmitted to computer 18 on which the image analysis software program is executing. As discussed more fully herein, the image analysis software program decomposes the image into its red, green and blue components, calculates differences between the red, green and blue components, and combines the differences to form a combined image.

FIG. 3 is a block diagram depicting the major steps performed by the image analysis software used in the system 10 of the present invention. At block 302, one to n images (where n is a positive integer greater than 1) of a sample at different polarization angles are acquired as uncompressed image files. At block 304, each image is decomposed to an m-dimensional matrix, or reference color space, that quantizes the color information in the image (m is any positive integer). One method is to map the image information to a reference color space using color models such as RGB or HSV. At block 306, the m-dimensional matrix is further reduced to a series of 2-dimensional matrices (usually representing the individual axes or channels of the color model). If the color model is RGB, three 2-dimensional matrices can be extracted representing the red, green and blue color channels. At block 308, the matrices are submitted to a background correction filter. Background correction is applied to each channel matrix to compensate for low frequency spatial variations that often dominate the raw images (such as light gradients or variations in the matrix of the sample). In contrast, the objects of interest are crystals with sharp edges and small dimensions that represent high frequency spatial variations of the image. The process for extracting the color signals exploits this characteristic frequency difference. At block 310, the background corrected matrix for each channel is integrated with the matrices derived from other polarization images to produce a new matrix in which birefringent signals are amplified. At block 312, the ensemble of matrices is reconstructed to produce the final digitally enhanced color image.

Figure 4:
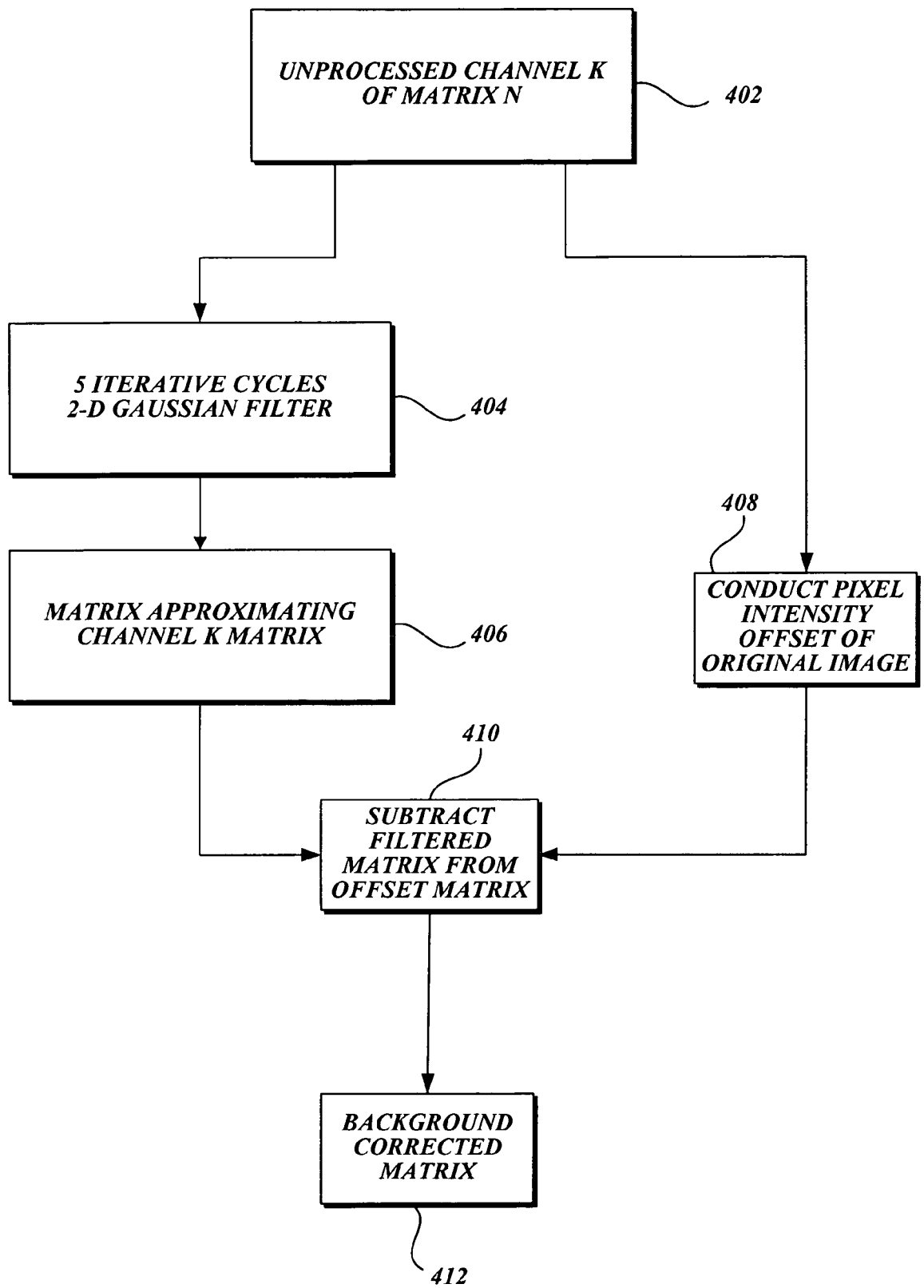
FIG. 4 is a block diagram that shows one form of background correction.

FIG. 4 is a block diagram that shows one form of background correction. At block 402, an image in the form of an unprocessed channel k of matrix n is provided. At block 404 the matrix is passed through five iterative cycles of a 2-D Gaussian filter to form a matrix approximating the background for channel k of matrix n at block 406. The Gaussian filter produces a series of increasingly blurred images of the channel in which the high frequency objects (such as crystal edges) are ever more deemphasized. The 2-D Gaussian convolution of the images is performed by first convolving with a 1-D Gaussian in the x direction and then convolving with another 1-D Gaussian in the y direction. For each image axis a Gaussian filter with sigma equal to 20 and mask of 1×40 pixels is used.

At block 408, a pixel intensity offset of the original image is conducted in which the brightness of each pixel is increased by a constant amount. The offset matrix ensures that the subsequent subtraction does not produce negative values (or truncations) in the matrix. At block 410, the final Gaussian filtered matrix is subtracted from the offset matrix yielding a new background corrected matrix at block 412. The background in the background corrected matrix has been flattened and the birefringent signal of the crystals emphasized.

Figure 5:
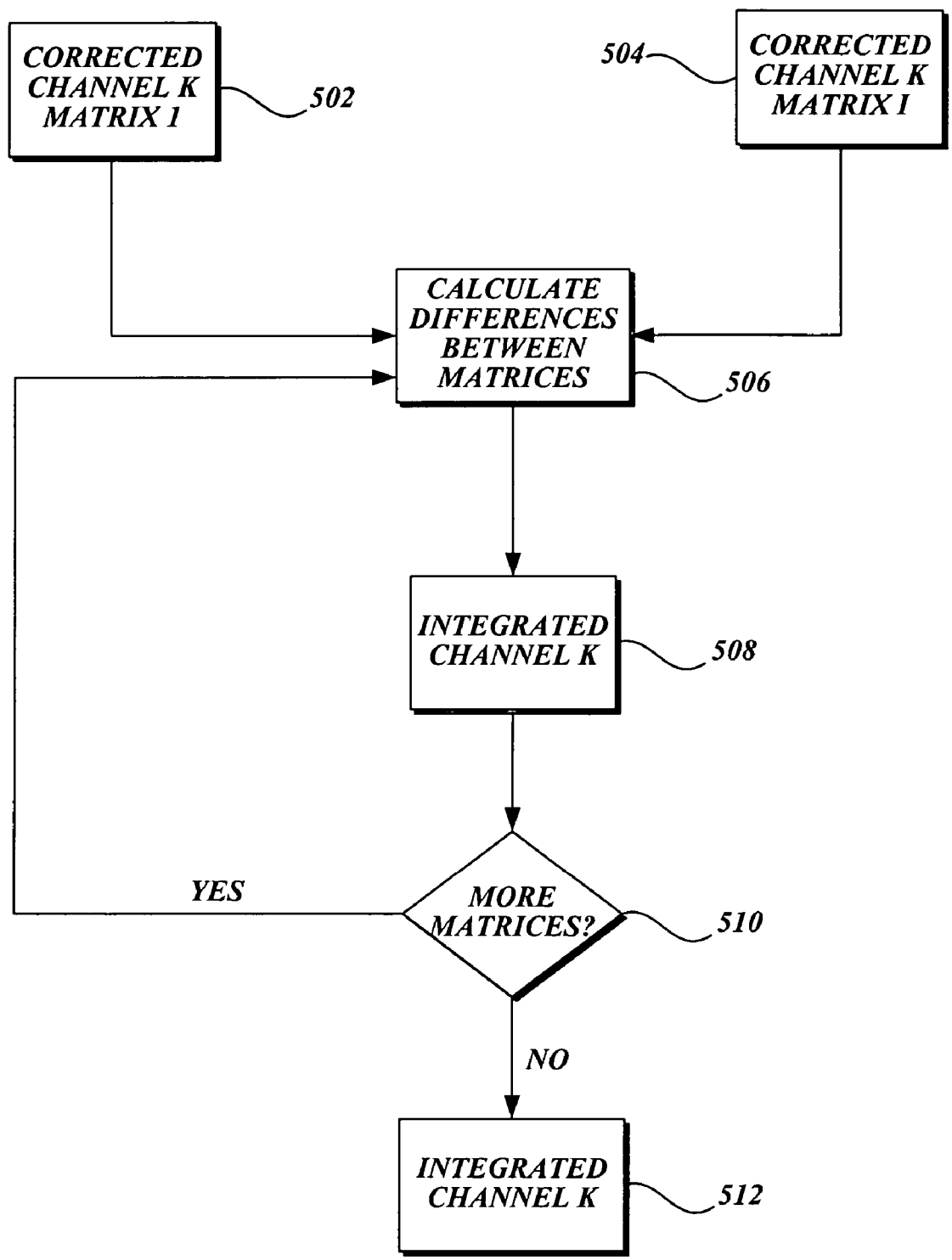
FIG. 5 is a block diagram showing one form of signal manipulation to integrate matrices representing different images of the same sample.

FIG. 5 is a block diagram showing one form of signal manipulation to integrate matrices representing different images of the same sample. At block 502, a corrected channel k matrix 1 is provided. At block 504, a corrected channel k matrix i is provided. At block 506, each pixel value in channel k matrix 1 is subtracted from the corresponding pixel position in channel k matrix i (where i is an integer that is less than the number of images). Truncations are avoided in the difference calculation by using absolute differences between the two channels. At block 508, the resulting set of matrices are integrated. At block 510, if there are more matrices then the process of signal manipulation is repeated with the additional matrices. If there are no additional matrices, at block 510 all matrices of a given channel are combined into an integrated channel at block 512.

Figure 6:
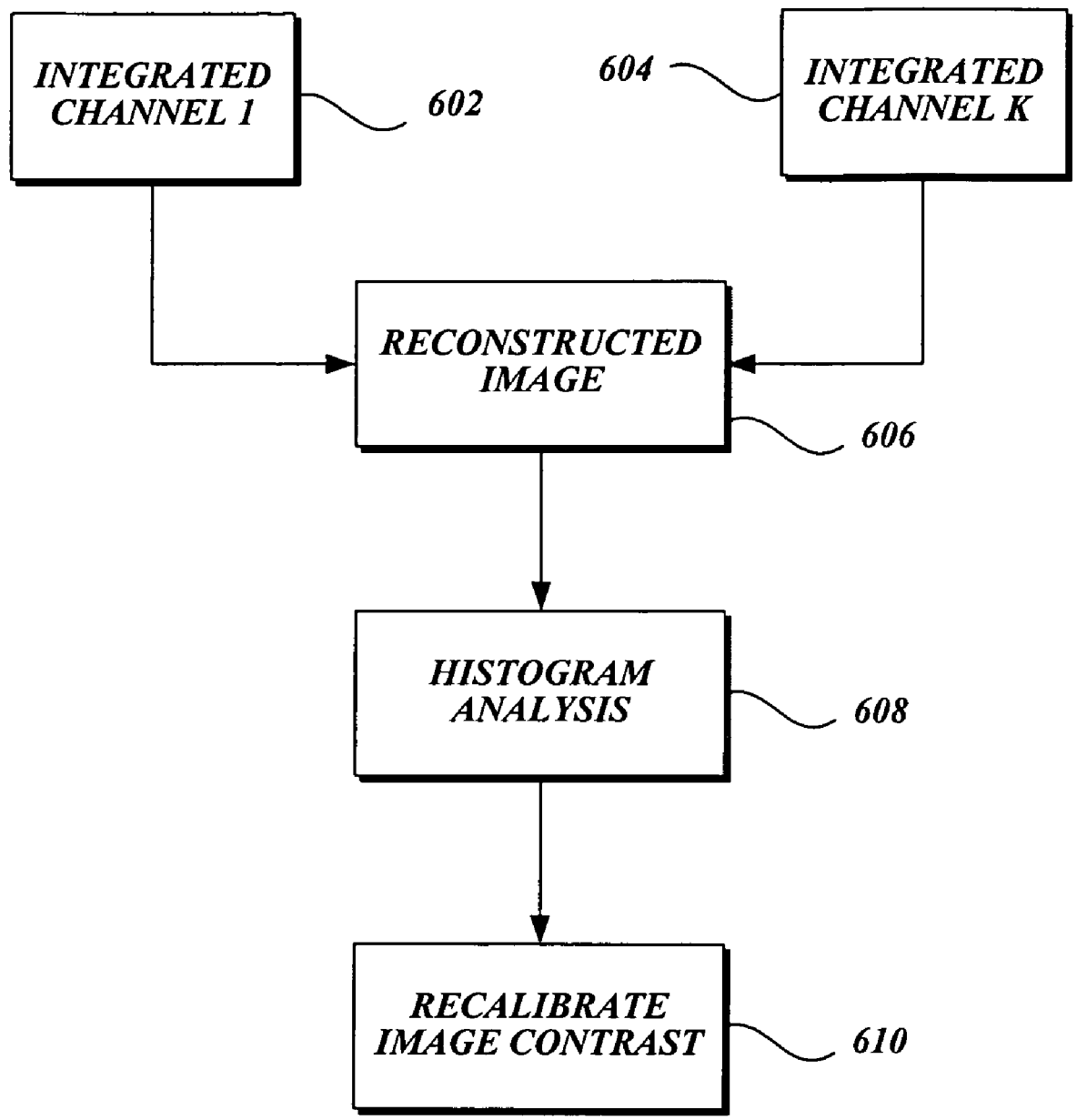
FIG. 6 is a block diagram showing the reconstruction of images from integrated matrices.

FIG. 6 is a block diagram showing the reconstruction of images from integrated matrices. At block 602, an integrated channel 1 is provided. At block 604, an integrated channel k is provided. At block 606, integrated channel matrices (1 through k) resulting from the difference calculations, described at block 506 of FIG. 5, are recombined to produce a reconstructed color enhanced image. At block 608, a histogram analysis of the reconstructed image is conducted (and typically shows that the pixel values are biased towards low values). At block 610, a final manipulation is performed in which the contrast of the image is recalibrated. This step is used to present users with an image that is easier to interpret. Maximum and minimum pixel values are determined for the reconstructed image and then, for each pixel in the image, the pixel value is rescaled such that maximum contrast is achieved.

Figure 7:
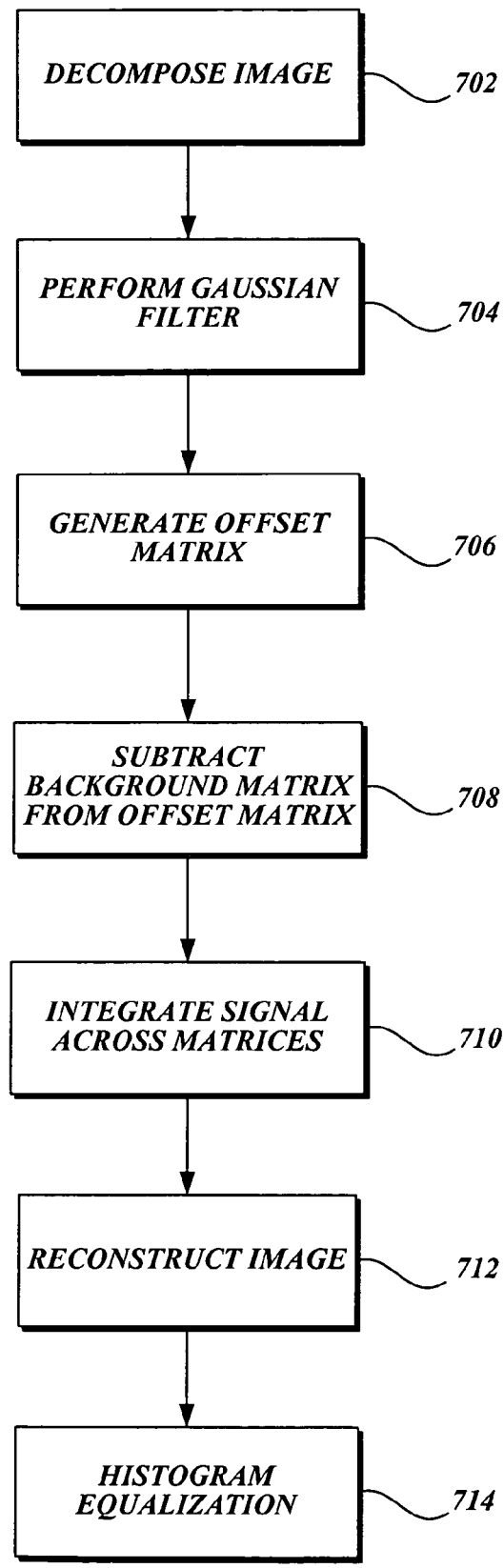
FIG. 7 shows the major steps performed by a representative example of an image analysis software program used in the system of the invention for generating images of crystals.

FIG. 7 shows the major steps performed by a representative example of an image analysis software program used in the systems of the invention for generating images of crystals. All functions in bold face type are MATLAB® functions. At block 702, image decomposition is performed by first using imread to transform the input image to an m-dimensional matrix and then extracting a 2-dimensional submatrix. At block 704, two functions are used to set up the Gaussian filter that yields a matrix approximating the signal of the background in the parent 2-dimensional matrix. First, at block 704, a Gaussian filter is specified using the function fspecial. The filter is applied to the parent matrix by using the function imfilter. At block 706, function imadd is used to generate an offset matrix. At block 708, function imabsdiff is used to subtract the background matrix from the offset matrix yielding a background corrected matrix. At block 710, integration of the signal across matrices is accomplished by using function imabsdiff or function imadd. At block 712, reconstruction of an image is accomplished by using function cat. At block 714, the reassembled image is optimized for contrast using the functions stretchlim and imadjust to produce the final image.

In another aspect, the present invention provides computer-implementable methods for visualizing a birefringent crystal. The methods of this aspect of the invention include the steps of: (a) recording a first visual image of a crystal that is viewed against a background, wherein the crystal is located between a first polarizing material and a second polarizing material, and wherein light that is used to illuminate the crystal to produce the first visual image travels through the first polarizing material, then through the crystal, then through the second polarizing material; (b) rotating the first or second polarizing materials by an amount about an axis of rotation, wherein the axis of rotation is at a 90° angle to the plane of the rotated polarizing material, and recording a second visual image of the crystal, wherein light that is used to illuminate the crystal to produce the second visual image travels through the first polarizing material, then through the crystal, then through the second polarizing material; and (c) combining the first visual image and the second visual image, to yield a combined image wherein the contrast of the crystal against the background is greater than in the first or second visual images.

Some computer-implementable methods for visualizing a birefringent crystal include the following steps: (a) recording a first visual image of a crystal that is viewed against a background, wherein the crystal is located between a first polarizing material and a second polarizing material, and wherein light that is used to illuminate the crystal to produce the first visual image travels through the first polarizing material, then through the crystal, then through the second polarizing material; and (b) rotating the first or the second polarizing material by an amount around an axis of rotation that is at a 90° angle to the plane of the rotated polarizing material, and recording a second visual image of the crystal, wherein light that is used to illuminate the crystal to produce the second visual image travels through the first polarizing material, then through the crystal, then through the second polarizing material, wherein (1) the first image is decomposed into a first image first color and a first image second color, and the second image is decomposed into a second image first color and a second image second color, wherein the first image first color is the same as the second image first color, and the first image second color is the same as the second image second color; (2) the first image first color is compared to the second image first color to yield a first color difference, and the first image second color is compared to the second image second color to yield a second color difference; and (3) the first color difference and the second color difference are combined to yield a composite image wherein the contrast of the crystal against the background is greater than in the first or second visual images.

Some computer-implementable methods for visualizing a birefringent crystal include the following steps: (a) recording a first visual image of a crystal that is viewed against a background, wherein the crystal is located between a first polarizing material and a second polarizing material, and wherein light that is used to illuminate the crystal to produce the first visual image travels through the first polarizing material, then through the crystal, then through the second polarizing material; and (b) rotating both the first or second polarizing materials by an amount about the same axis of rotation, wherein the axis of rotation is at a 90° angle to the plane of the rotated polarizing material, and recording a second visual image of the crystal, wherein light that is used to illuminate the crystal to produce the second visual image travels through the first polarizing material, then through the crystal, then through the second polarizing material, wherein (1) the first image is decomposed into a first red image, a first blue image and a first green image, and the second image is decomposed into a second red image, a second blue image and a second green image; (2) the first red image is compared to the second red image to yield a red image composite, the first blue image is compared to the second blue image to yield a blue image composite, and the first green image is compared to the second green image to yield a green image composite; and (3) the blue image composite, the red image composite and the green image composite are combined to yield a composite image wherein the contrast of the crystal against the background is greater than in the first or second visual images.

The systems of the present invention can be used to practice the methods of the invention.

In some embodiments of the methods of the present invention the crystal is disposed within a birefringent material. The first and second polarizing materials can be moved by the same amount about the same axis of rotation, or the first and second polarizing materials can be moved by different amounts about the same axis of rotation. The first and second polarizing materials can be rotated, for example, by a motor-driven assembly, or, for example, the first and second polarizing materials can be rotated manually. The first and second polarizing materials are typically moved together when both polarizing materials are linear polarizers that have been brought to extinction. An example of a situation wherein the first and second polarizing materials are both moved, but the movement of the first and second polarizing materials is not synchronized, is to compensate for polarization caused by the crystallization tray. If the first polarizing material is a circular polarizing material, then the first polarizing material is typically not rotated, and only the second polarizing material (being a linear polarizer) is rotated.

In some embodiments of the methods of the present invention the first visual image is recorded when the first and second polarizing materials are oriented at extinction.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A computer-implementable system for generating images of crystals, the system comprising:
   (a) a light source;
   (b) a rotatable first polarizing material;
   (c) a rotatable second polarizing material;
   (d) a light-capturing device; and
   (e) a software program executable on the computer-implementable system for analyzing electrical signals from the light capturing device, wherein, in operation,
      (1) light from the light source passes through the first polarizing material, then passes through a protein sample located between the first polarizing material and the second polarizing material, then passes through the second polarizing material and impinges on the light-capturing device to generate multiple images of the protein sample after the first polarizing material has rotated, after the second polarizing material has rotated, or after both polarizing materials have rotated, the multiple images each comprising a red component, a green component and a blue component, in the form of an electrical signal that is transmitted to a computing device on which the software program is executing; and
      (2) the software program represents the multiple images as multiple matrices, decomposes the multiple images into their red, green and blue components, calculates differences between the red, green and blue components by comparing information in one matrix with corresponding information in another matrix, repeats the act of differences calculation for a number of matrices, and combines the differences to form a combined image.

2. A system of claim 1 wherein the light source emits light having a wavelength in the range of from 400 nm to 800 nm.

3. A system of claim 1 wherein the first polarizing material is one of a circular light polarizing material or a linear light polarizing material.

4. A system of claim 1 wherein the first polarizing material consists essentially of a linear light polarizing material.

5. A system of claim I wherein the first polarizing material is rotatable around an axis of rotation that is at a 90 degree angle to the plane of the first polarizing material.

6. A system of claim 1 wherein the second polarizing material consists essentially of a linear light polarizing material.

7. A system of claim 1 wherein the first polarizing material is rotated by a first motor, and the second polarizing material is rotated by a second motor.

8. A system of claim 1 wherein the second polarizing material is rotatable around an axis of rotation that is at a 90 degree angle to the plane of the second polarizing material.

9. A system of claim 1 wherein the light-capturing device is a camera.

10. A system of claim 1 wherein the software program:
(1) acquires from 1 to n sample images;
(2) decomposes each of the sample images;
(3) reduces the decomposed sample images to a series of two dimensional matrices;
(4) submits each of the matrices to background correction; and
(5) integrates the background corrected matrices to construct an enhanced image of the protein sample.

11. A computer-implementable method for visualizing a birefringent crystal, the method comprising the steps of:
(a) recording a first visual image of a protein crystal that is viewed against a background, wherein the protein crystal is located between a first polarizing material and a second polarizing material, and wherein light that is used to illuminate the protein crystal to produce the first visual image travels through the first polarizing material, then through the protein crystal, then through the second polarizing material;
(b) rotating the first, second, or both polarizing materials by an amount about an axis of rotation, wherein the axis of rotation is at a 90 degree angle to the plane of the rotated polarizing material, and recording multiple visual images of the protein crystal, wherein light that is used to illuminate the protein crystal to produce the multiple visual images travels through the first polarizing material, then through the protein crystal, then through the second polarizing material; and
(c) combining the first visual image and the multiple visual images, to yield a combined image by representing the first visual image and the multiple visual images as multiple matrices with channels, comparing information in the various channels of one matrix to corresponding information in the various channels of another matrix, and repeating the act of comparison for a number of matrices, wherein the contrast of the protein crystal against the background is greater than in the first or second visual images.

12. The method of claim 11 wherein the protein crystal is disposed within a birefringent material.

13. The method of claim 11 wherein the first and second polarizing materials are moved by the same amount about the same axis of rotation.

14. The method of claim 11 wherein the first visual image is recorded when the first and second polarizing materials are oriented at extinction.

15. The method of claim 11 wherein the first and second polarizing materials are rotated by a motor-driven assembly.

16. The method of claim 11 wherein the first and second polarizing materials are rotated manually.

17. A computer-implementable method for visualizing a birefringent crystal, the method comprising the steps of:
(a) recording a first visual image of a protein crystal that is viewed against a background, wherein the protein crystal is located between a first polarizing material and a second polarizing material, and wherein light that is used to illuminate the protein crystal to produce the first visual image travels through the first polarizing material, then through the protein crystal, then through the second polarizing material; and
(b) rotating the first, second, or both polarizing materials by an amount around an axis of rotation that is at a 90 degree angle to the plane of the rotated polarizing material, and recording multiple visual images of the protein crystal, wherein light that is used to illuminate the protein crystal to produce the multiple visual images travels through the first polarizing material, then through the protein crystal, then through the second polarizing material, wherein
(1) the first visual image is decomposed into a first image first color and a first image second color, and the multiple visual images are decomposed into multiple visual images first colors and multiple visual images second colors;
(2) the first visual image first color is compared to one of the multiple visual images first colors to yield a first color difference, and the first image second color is compared to one of the multiple visual images second colors to yield a second color difference; and
(3) the first color difference and the second color difference are combined to yield a composite image wherein the contrast of the protein crystal against the background is greater than in the first or second visual images.

18. The method of claim 17 wherein the first and second colors are selected from the group consisting of red, blue and green.

19. The method of claim 17 wherein the visual image are corrected for background.

20. A computer-implementable method for visualizing a birefringent crystal, the method comprising the steps of:
(a) recording a first visual image of a protein crystal that is viewed against a background, wherein the protein crystal is located between a first polarizing material and a second polarizing material, and wherein light that is used to illuminate the protein crystal to produce the first visual image travels through the first polarizing material, then through the protein crystal, then through the second polarizing material; and
(b) rotating both the first, second, or both polarizing materials by an amount about the same axis of rotation, wherein the axis of rotation is at a 90 degree angle to the plane of the rotated polarizing material, and recording multiple visual images of the protein crystal, wherein light that is used to illuminate the protein crystal to produce the multiple visual images travels through the first polarizing material, then through the protein crystal, then through the second polarizing material, wherein
(1) the first visual image is decomposed into a first red image, a first blue image and a first green image, and the multiple visual images are decomposed into multiple red images, multiple blue images, and multiple green images;
(2) the first red image is compared to one of the multiple red images to yield a red image composite, the first blue image is compared to one of the multiple blue images to yield a blue image composite, and the first green image is compared to the one of the multiple green images to yield a green image composite; and (3) the blue image composite, the red image composite and the green image composite are combined to yield a composite image wherein the contrast of the protein crystal against the background is greater than in the first or second visual images.

21. The method of claim 20 wherein the first polarizing mnaterial and the second polarizing material are components of a microscope.

* * * * *

UNITED STATES PATENT AND TRADEMARK OFFICE
CERTIFICATE OF CORRECTION

PATENT NO. : 7,462,237 B2  Page 1 of 1
APPLICATION NO. : 11/170758
DATED : December 9, 2008
INVENTOR(S) : P. Nollert-von Specht et al.

It is certified that error appears in the above-identified patent and that said Letters Patent is hereby corrected as shown below:

| COLUMN | LINE | ERROR |
|---|---|---|
| 10 (Claim 5) | 65 | "claim I" should read --claim 1-- |
| 14 (Claim 21) | 2 | "mnaterial" should read --material-- |

Signed and Sealed this

Fourth Day of August, 2009

JOHN DOLL
*Acting Director of the United States Patent and Trademark Office*